United States Patent [19]

McLees

[11] Patent Number: 5,106,855
[45] Date of Patent: Apr. 21, 1992

[54] METHOD FOR THE TREATMENT OF GLAUCOMA

[75] Inventor: Byron D. McLees, Cincinnati, Ohio

[73] Assignee: Merrell Dow Pharmaceuticals Inc., Cincinnati, Ohio

[21] Appl. No.: 742,537

[22] Filed: Aug. 8, 1991

Related U.S. Application Data

[63] Continuation of Ser. No. 453,569, Dec. 20, 1989, abandoned.

[51] Int. Cl.$^5$ .............................................. A61K 31/44
[52] U.S. Cl. ................................... 514/317; 514/331; 514/913
[58] Field of Search .................... 514/317, 331, 913

[56] References Cited

U.S. PATENT DOCUMENTS 5,011,846  4/1991  Gittos et al. ...................... 514/294

FOREIGN PATENT DOCUMENTS 319962  12/1987  European Pat. Off. .
61-204124  3/1985  Japan .

OTHER PUBLICATIONS

Effects of a 5HT$_2$ Antagonist (ICI 169,369) on Human Pupillary Responses, *Br. J. Clin. Pharmacol.*, 26:625P, (1988).

Primary Examiner—Frederick E. Waddell
Assistant Examiner—Zohreh A. Fay
Attorney, Agent, or Firm—J. Michael Dixon

[57] ABSTRACT

The present invention is directed to a method for the treatment of glaucoma and to pharmaceutical preparations suitable in such a method.

2 Claims, No Drawings

METHOD FOR THE TREATMENT OF GLAUCOMA

CROSS-REFERENCE TO RELATED APPLICATION

This is a continuation of application Ser. No. 07/453,569, filed Dec. 20, 1989, now abandoned.

The present invention is directed to a method for the treatment of glaucoma. Another aspect of this invention is directed to new ophthalmic preparations which are useful in the treatment of glaucoma.

Glaucoma is a disorder in which elevated intraocular pressure damages the optic nerve thereby producing blindness. The are two major types of glaucoma, chronic open-angle and acute narrow-angle.

Intraocular pressure is controlled by the dynamics of aqueous humor. The aqueous humor is derived from blood by a process of secretion and ultrafiltration in the ciliary body. Aqueous humor then passes from the posterior chamber of the eye, through the pupil to fill the anterior chamber, which is the space between the back of the cornea and the plane of the iris and pupil. The aqueous humor is reabsorbed through the trabecular meshwork, located in the angle between the cornea and the iris. The aqueous humor then enters the canal of Schlemm so that it may be drained away from the eye.

In chronic open-angle glaucoma, the most common type, a defect in aqueous humor reabsorption exists at the level of the trabecular meshwork. Intraocular pressure rises above its normal maximum of 21 mm HG due to the presence of excess aqueous humor. In acute narrow-angle glaucoma, dilation of the iris leads to the physical blockade of the entrance to the canal of Schlemm.

In accordance with the present invention, it has been discovered that these types of glaucoma can be treated by the administration of one of the following compounds

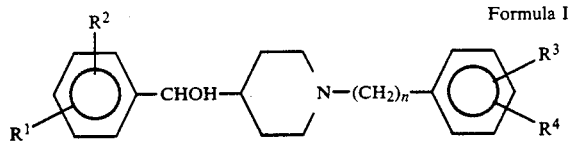

Formula I in which:
each of $R^1$, $R^2$, $R^3$, and $R^4$ is independently selected from the group consisting of hydrogen, $C_{1-6}$ alkyl, halogen, trifluoromethyl, hydroxy, $C_{1-6}$ alkoxy, or an amino group; n is 2, 3, or 4; and the pharmaceutically acceptable acid addition salts thereof.

As used in this application:

a) The term "$C_{1-6}$ alkyl" refers to a straight chain or branched alkyl group containing up to 6 carbon atoms. Representative examples of suitable alkyl groups include, methyl, ethyl, propyl, isopropyl, n-butyl, t-butyl, pentyl, hexyl, cyclopropyl, and cyclopentyl. Methyl and ethyl are currently preferred.

b) The term "halogen" refers to a fluorine, bromine, chlorine or iodine atom. Fluorine and chlorine are currently preferred.

c) The term "$C_{1-6}$" alkoxy refers to a straight chain or branched alkoxy group containing up to 6 carbon atoms. Representative examples of suitable alkoxy groups include methoxy, ethoxy, propoxy, isopropoxy, butoxy, pentoxy, and hexyloxy.

d) The term "hydroxy" in this application refers to the following substituent —OH.

e) The term "amino" refers to "—$NH_2$".

f) The term "patient" as used herein is taken to mean warm-blooded animals, such as mammals, for example, dogs, rats, mice, cats, guinea pigs, horses, cattle, sheep and primates, including humans, and g) The term "glaucoma" should be construed as referring to either chronic open angle glaucoma or acute narrow angle glaucoma.

The expression "pharmaceutically acceptable acid addition salts" is intended to apply to any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid and 2-hydroxyethane sulfonic acid.

Some of the compounds represented by Formula I exist as optical isomers. Any reference in this application to the compounds of Formula I, is meant to encompass a specific isomer or a mixture of isomers.

In those instances where $R^1$-$R^4$ are other than hydrogen, the substituents may be located at any position of the phenyl ring (i.e., meta, para, or ortho). Para is currently preferred for monosubstituted phenyl moieties. The 2,3-, 2,4- 2,5-, 3,4-, or 3,5-disubstituted phenyl moieties are also embraced herein. $R^1$, $R^2$, $R^3$, and $R^4$ can each be the same or different substituents.

It is currently preferred for n to be either 2 or 3, with 2 being most preferred. It is also currently preferred for $R^3$ and $R^4$ to be hydrogen.

Representative examples of preferred compounds include:
1) α-phenyl-1-(2-phenethyl)-4-piperidine methanol;
2) α-phenyl-1-(3-phenylpropyl)-4-piperidine methanol;
3) α-(4-methylphenyl)-1-(2-phenethyl)-4-piperidine methanol;
4) α-(4-methoxyphenyl)-1-(2-phenethyl)-4-piperidine methanol;
5) α-(3,5-dimethylphenyl)-1-(2-phenethyl)-4-piperidine methanol;
6) α-(3-(trifluoromethyl)phenyl)-1-(2-phenethyl)-4-piperidine methanol;
7) α-(2,3-dimethoxyphenyl)-1-(2-phenethyl)-4-piperidine methanol;
8) α-(4-fluorophenyl)-[1-(2-phenylethyl)-4-piperidinyl]-methanol;
9) α-phenyl-[1-(4-phenylbutyl)-4-piperidinyl]-methanol;
10) α-(3,4-dimethoxyphenyl-[1-(2-phenylethyl)-4-piperidinyly]-methanol;
11) α-phenyl-[1-(4-aminophenylethyl)-4-piperidinyl]-methanol;
12) α-phenyl[1-(4-methoxyphenylethyl)-4-piperidinyl]-methanol;

13) α-(4-methoxyphenyl)-[1-(4-methoxyphenylethyl)-4-piperidinyl]-methanol;

14) α-(2,3-dimethoxyphenyl)-[1-(4-methoxyphenylethyl)- 4-piperidinyl]-methanol;

15) α-phenyl-[1-(4-methoxyphenylethyl)-4-piperidinyl]-methanol;

16) α-phenyl-[1-(4-fluorophenylethyl)-4-piperidinyl]-methanol;

17) α-(4-hydroxyphenyl)-[1-(2-phenylethyl)-4-]-methanol;

18) α-(3,4-dihydroxyphenyl)-[1-(2-phenylethyl)-4-piperidinyl]-methanol;

19) α-(3,4-dichlorophenyl)-1-(2-phenylethyl)-4-piperidine methanol.

The compounds of Formula I, their methods of preparation and their use as serotonin 5HT$_2$ antagonists are known in the art. European Patent Application 0 208 235 discloses these compounds and several methods for preparing these compounds.

It has been discovered that the compounds of Formula I decrease intraocular pressures and are therefore useful in the treatment of glaucoma. The exact mechanism by which these compounds decrease intraocular pressure is not fully understood. However it has been learned that these compounds produce constriction of the sphincter muscle of the iris. Constriction of this muscle produces miosis (i.e. constriction of the pupil). Several other drugs which are known to be useful in the treatment of glaucoma also produce this effect upon the sphincter muscle of the iris. These drugs include pilocarpine, physostigmine, and echothiphate.

In acute narrow angle glaucoma, the iris physically blocks the entrance to the Canal of Schlemm. Contraction of the sphincter muscle of the iris ends this physical blockade and allows the outflow of aqueous humor from the eye. In chronic open angle glaucoma, there is no direct blockade of the Canal of Schlemm, rather there is a defect in the manner in which the trabeculae meshwork reabsorbs the aqueous humor. Contraction of the sphincter muscle of the iris improves the reabsorption of aqueous humor through the trabeculae meshwork into the Canal of Schlemm.

If desired, the compounds of Formula I can be administered systemically in order to lower intraocular pressures. They can be administered either orally or parenterally. The quantity of compound required to produce this ocular hypotensive effect will vary widely depending upon the particular compound utilized, the patient, the route of administration, the severity of the patient's glaucoma, the presence of other underlying disease states in the patient, and other medications which are being administered concurrently to the patient. Generally though, if the compounds are being administered systemically, than a patients' glaucoma will respond to a dosage range of from about 0.1 mg/kg/ day to about 100 mg/kg/day. This dosage will typically be administered from 1 to 4 times daily.

The compounds of Formula I can be compounded into a variety of systemic dosage forms, such as for example, tablets, capsules, solutions, elixirs, sterile solutions for injection and sustained release preparations. Methods for producing these dosage forms are well known in the art and are disclosed in European Patent Application 0208235.

The compounds can also be administered topically via ophthalmic dosage forms such as, for example, ophthalmic drops, ophthalmic ointments, and ophthalmic disks. The ophthalmic drops of the present invention should contain from 0.1-10% w/w of one of the compounds of Formula I. Typically, it will be dissolved in a buffered, isotonic solution containing antimicrobial preservative agents. The ophthalmic ointments will also generally contain from 0.1-10% w/w of one of the compounds of Formula I admixed with a suitable base, such as white petrolatum and mineral oil, along with antimicrobial preservatives. The ophthalmic disks will typically be constructed so as to contain a core of active ingredient surrounded by a polymer matrix such as, for example, a hydrophobic ethylene/vinyl acetate copolymer. Specific methods of compounding these dosage forms, as well as appropriate ophthalmic pharmaceutical carriers are known in the art. REMINGTON PHARMACEUTICALS SCIENCES, 16th Ed. Mack Publishing Co. (1980).

Typically, the ophthalmic drops or ophthalmic ointments will be administered from 1 to 4 times daily. The ophthalmic disks will be administered weekly.

What is claimed is:

1. A method for the treatment of glaucoma comprising administering to a patient with glaucoma a compound of the formula:

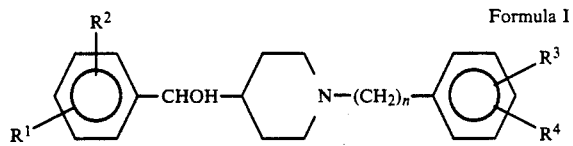

Formula I in which:
each of $R^1$, $R^2$, $R^3$, and $R^4$ is independently selected from the group consisting of hydrogen, a $C_{1-6}$ alkyl, halogen, trifluoromethyl, hydroxy, $C_{1-6}$ alkoxy, or an amino group; n is 2, 3, or 4; and the pharmaceutically acceptable acid addition salts thereof, in an amount sufficient to lower intraoccular pressure.

2. The method of claim 1, wherein said compound is α-phenyl-1-(2-phenethyl)-4-piperidine methanol.

* * * * *